United States Patent [19]

Wolff

[11] Patent Number: 5,134,061
[45] Date of Patent: Jul. 28, 1992

[54] PHOTOGRAPHIC RECORDING MATERIAL

[75] Inventor: Erich Wolff, Solingen, Fed. Rep. of Germany

[73] Assignee: Agfa Gevaert Aktiengesellschaft, Leverkusen, Fed. Rep. of Germany

[21] Appl. No.: 671,992

[22] Filed: Mar. 18, 1991

Related U.S. Application Data

[63] Continuation of Ser. No. 438,747, Nov. 17, 1989, abandoned.

[30] Foreign Application Priority Data

Dec. 2, 1988 [DE] Fed. Rep. of Germany ....... 3840619

[51] Int. Cl.$^5$ .............................................. G03C 1/005
[52] U.S. Cl. .................................... 430/638; 430/543; 430/546; 430/222; 430/512; 430/564; 430/566; 430/551; 430/553; 430/631; 430/559
[58] Field of Search ............... 430/543, 546, 222, 512, 430/564, 566, 551, 553, 631, 638, 559, 636

[56] References Cited

U.S. PATENT DOCUMENTS

| | | | |
|---|---|---|---|
| 3,892,576 | 7/1975 | Van Poucke et al. | 430/556 |
| 4,080,209 | 3/1978 | Mununoki et al. | 430/546 |
| 4,266,019 | 5/1981 | Van Poucke et al. | 430/556 |
| 4,639,413 | 1/1987 | Kawagishi | 430/546 |
| 4,731,320 | 3/1988 | Sasaki et al. | 430/546 |
| 4,837,136 | 6/1989 | Iohijima et al. | 430/546 |

Primary Examiner—Charles L. Bowers, Jr.
Assistant Examiner—Thomas R. Neville
Attorney, Agent, or Firm—Connolly & Hutz

[57] ABSTRACT

Photographically useful organic compounds containing secondary-branched alkyl radicals with at least 15 C atoms corresponding to formula I have a low melting point, good solubility in oil formers and a low tendency towards crystallization which makes them particularly suitable for photographic applications.

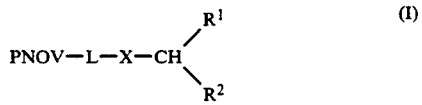

In formula I:

PNOV is the residue of a photographically useful organic compound, for example a coupler or oil former;
L is a chemical bond or a link between PNOV and X;
X represents —O—, —S—, —SO—, —SO$_2$—, —NH—, —NR— (R=alkyl or acyl), —CO— or alkylidene;
R$^1$ and R$^2$ are unbranched alkyl radicals containing at least 6 C atoms, with the proviso that R$^1$ and R$^2$ together contain at least 14 C atoms and, where X represents —CO— or —CH$_2$, at least 17 C atoms.

4 Claims, No Drawings

PHOTOGRAPHIC RECORDING MATERIAL

CROSS REFERENCE TO RELATED APPLICATION

This application is a file wrapper continuation of U.S. application Ser. No. 07/438,747 filed Nov. 17, 1989, now abandoned, by Erich Wolff for Photogrpahic Recording Material.

This invention relates to a photographic recording material containing photographic "building blocks" incorporated in non-diffusing form. These building blocks are photographically useful organic compounds of various kinds containing secondary-branched alkyl radicals. By virtue of this particular structure, the building blocks according to the invention have a low melting point, good solubility in oil formers and a low tendency towards crystallization, which makes them particularly suitable for use in photography, particularly with a view to obtaining high maximal color density, steep gradation, high color yield (important for reducing the amount of silver applied), particularly where processing is carried out in color developers free from benzyl alcohol, and improved stability to variations in the processing conditions. By virtue of the properties mentioned above, the building blocks according to the invention are also suitable for use in high-speed processing.

In the production of photographic silver halide emulsion layers and other hydrophilic colloid layers of a photographic silver halide material, it is often necessary to use components, such as color couplers, masking compounds, white couplers, UV absorbers and the like, which are not diffusible in these hydrophilic colloid media, so that they do not migrate. To this end, the components are usually provided in their molecule with one or more ballast groups, for example a long-chain aliphatic group, such as an alkyl group, containing from 5 to 20 carbon atoms in a straight line. This ballast group gives the molecule a hydrophobic character and holds the components firmly in the original hydrophilic colloid layer.

The methods by which these non-diffusible components are incorporated in the photographic hydrophilic colloid layers involves numerous problems and many possibilities have been considered with a view to solving these problems.

A method typically used for incorporating these components in non-diffusing form in hydrophilic colloid mixtures, such as a gelatine-silver halide emulsion is to introduce one or more salt-forming groups, for example carboxy and/or sulfo groups, into the molecule of the said components, so that they can be dissolved in the hydrophilic colloid mixture in the form of their soluble alkali metal salts.

The introduction of these non-diffusible components containing salt-forming groups into aqueous hydrophilic colloid mixtures frequently presents a number of difficulties. Many of these components bearing sulfo and/or carboxyl groups are in fact not sufficiently soluble in the desired concentration of this alkaline solution, while others crystallize after a short time in these solutions or give rise to flocculation when the solution is mixed with the aqueous, hydrophilic colloidal medium. In addition, some compounds are only soluble in highly alkaline solutions which are too basic for use in the usual photosensitive silver halide material. Where highly alkaline solutions are used, the hydrophilic colloid mixture should be reacidified thereafter, so that flocculation can occur and inorganic salts are formed. Another problem affecting the use of these components is the presence of the water-solubilizing groups, particularly the sulfo groups, because these groups have a significant effect on the viscosity of the hydrophilic colloidal medium. For example, it is difficult to obtain reproducible viscosity values for hydrophilic colloid mixtures containing such components under the same conditions. Where compositions of the type in question are stored, their viscosity continues to change.

In another method which is described, for example, in DE-B-1 127 714, water-insoluble color couplers are dissolved in low-boiling solvents predominantly immiscible with water, such as ethyl acetate, methylene chloride, chloroform, etc., after which the solution formed is dispersed in the hydrophilic colloidal medium in the form of extremely fine droplets in the presence of a wetting agent or dispersant, after which the solvent is removed by evaporation, leaving behind a dispersion of a color coupler which is dispersed in the hydrophilic colloid mixture.

Another process is described in U.S. Pat. No. 2,322,027. In this process, a color coupler is dissolved in a high-boiling, oily solvent, such as tricresyl phosphate and di-n-butyl phthalate, after which the solution obtained is dispersed in the form of extremely fine droplets in the hydrophilic colloid mixture. The oil solvent is left behind in the mixture.

One of the advantages of the dispersion techniques described above is that it is possible to use components which do not contain any salt-forming groups. However, these processes also involve difficulties. In fact, the components which are intended to be incorporated in photographic, colloidal media from solutions in low-boiling or high-boiling organic solvents should be sufficiently soluble in those solvents and should be homogeneously dispersed in the colloidal media, i.e. both before and after application, to form a hydrophilic colloid layer of a photographic material, so that no crystallization of component occurs.

This requirement limits the number of components which are suitable for such applications. Various components containing one or more hydrophobic ballast groups are not sufficiently soluble in these organic low-boiling or high-boiling solvents or give rise to crystallization of the component either when the organic solution is dispersed in the hydrophilic colloidal medium or when the hydrophilic colloidal medium is applied to form a layer of a photographic material or when it is processed. In this way, the degree of dispersion is significantly reduced, resulting in an adverse effect on the sensitometric properties of the photographic material.

It has now been found that photographically useful organic compounds (building blocks) corresponding to general formula I are distinguished by low melting points, good solubility in various high-boiling solvents (oil formers), a low tendency towards crystallization and excellent digestion stability. In addition, the oil formers mentioned may be positively influenced in regard to their melting point or their dissolving power for other building blocks when they correspond to general formula I.

The present invention relates a photographic recording material comprising at least one photosensitive silver halide emulsion layer arranged on a layer support and, optionally, other non-photosensitive binder layers which, in a photosensitive or non-photosensitive layer, contains at least one photographically useful organic compound corresponding to general formula (I)

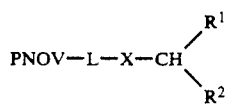

in which

PNOV is the residue of a photographically useful organic compound;

L is a chemical bond or a link between PNOV and X;

X represents —O—, —S—, —SO—, —SO$_2$—, —NH—, —NR— (R=alkyl or acyl), —CO— or alkylidene;

R$^1$ and R$^2$ may be the same or different and represent unbranched alkyl radicals containing at least 6 C atoms, with the proviso that R$^1$ and R$^2$ together contain at least 14 C atoms and, where X is —CO— or —CH$_2$—, at least 17 C atoms.

The link L is, for example, —O—, —CO—, —SO$_2$—, —NH—, —S—, alkylene, arylene or any combination thereof. Alkylene may be linear or branched and may preferably contain up to 6 C atoms. Arylene is preferably phenylene, optionally substituted, for example by halogen, alkyl, alkoxy or acylamino.

An alkylidene radical X contains from 1 to 6 C atoms for example; one example is —CH$_2$—. An alkyl radical R is, for example, methyl, ethyl or butyl; an acyl radical R is derived, for example, from alkane carboxylic acids containing up to 6 C atoms; one example is acetyl.

The building blocks according to the invention are low molecular weight, non-polymeric compounds; more particularly, R$^1$ and R$^2$ are not part of a polymer chain.

The effect of X and L together is that the secondary C atom (CH) bearing the unbranched alkyl radicals R$^1$ and R$^2$ is separated from the residue PNOV by at least one C atom or heteroatom.

The "photographically useful organic compound", of which the residue is represented by PNOV, is meant to be understood in the broadest sense of the term and encompasses all organic building blocks which may always be used for this purpose in photographic recording materials. These include both image-dye-producing compounds and also compounds which do not produce image dyes. More particularly, the compounds in question may be, for example, dyes of various kinds, couplable compounds of various kinds, particularly color couplers, white couplers, couplers capable of releasing a photographically active group (DIR couplers, DAR couplers and the like), smearing couplers, competitive couplers, developers, particularly color developers, antioxidants, reducing agents, electron donors, scavengers, oil formers, mordants, UV absorbers, whiteners, dye stabilizers, complexing agents (fixing agents), antistatic agents, compounds which increase covering power, fungicides, bactericides, formalin scavengers, plasticizers.

Image-dye-producing compounds include dye-producing compounds which are capable of releasing a diffusible dye and also color couplers, particularly cyan couplers, magenta couplers or yellow couplers.

Examples of "building blocks" according to the invention are given in the following:

Cyan couplers

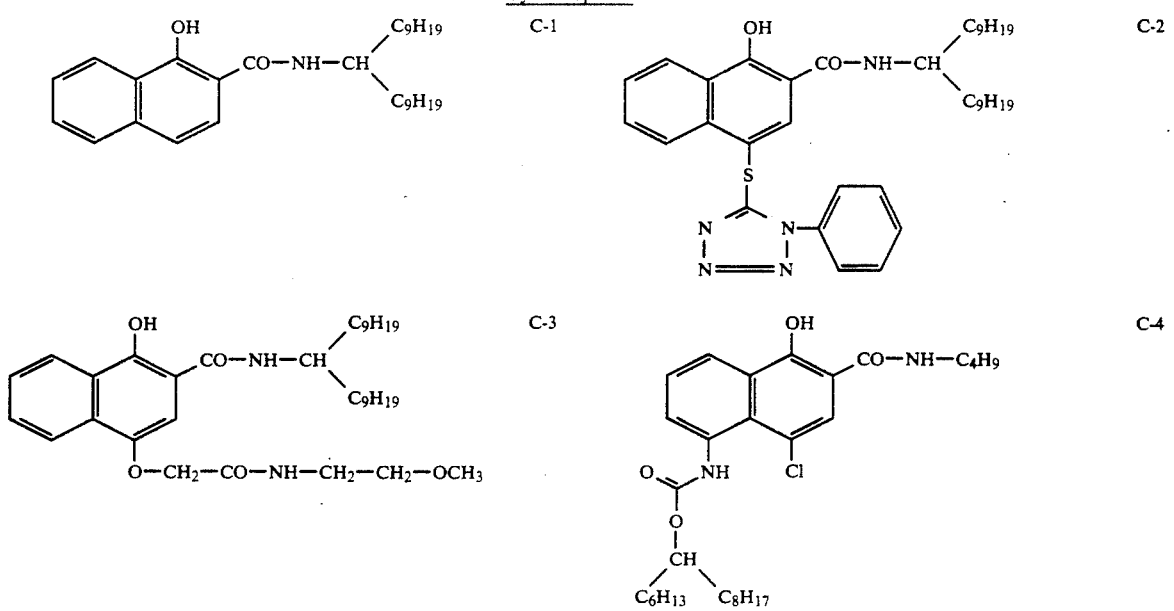

-continued
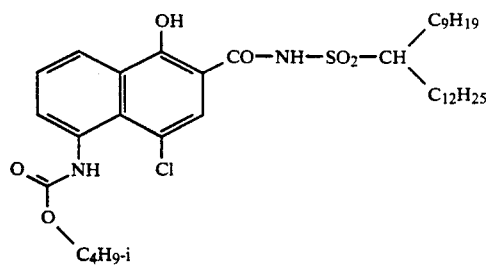
C-5
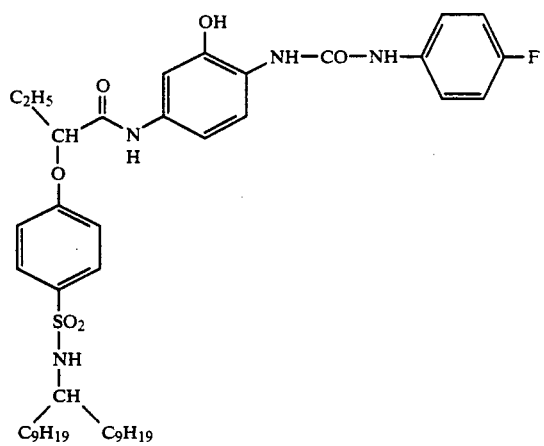
C-6
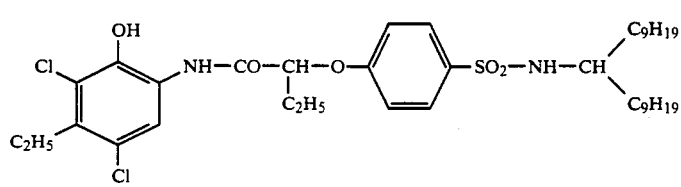
C-7
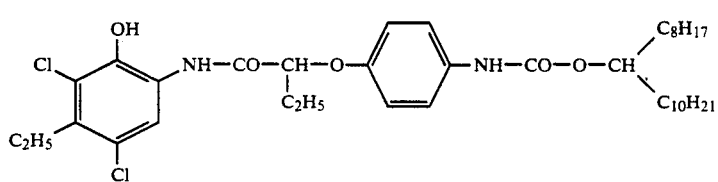
C-8
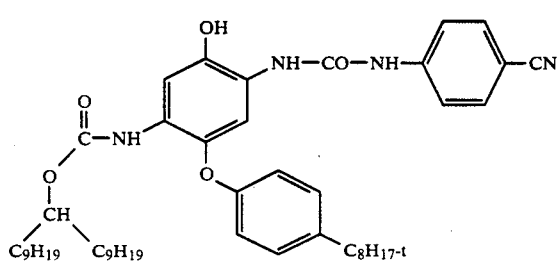
C-9
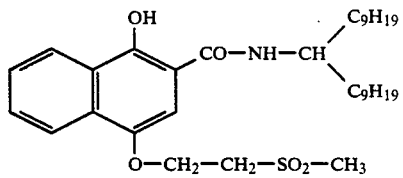
C-10
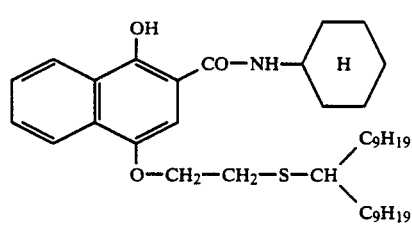
C-11
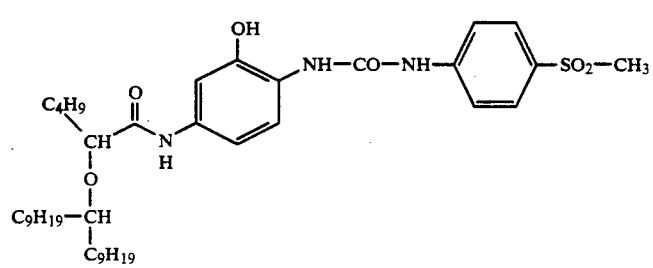
C-12

C-13
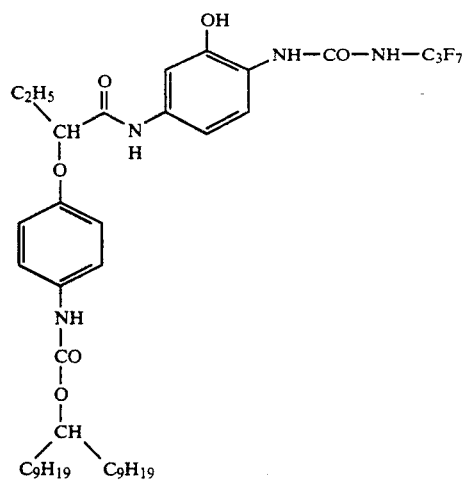
C-14
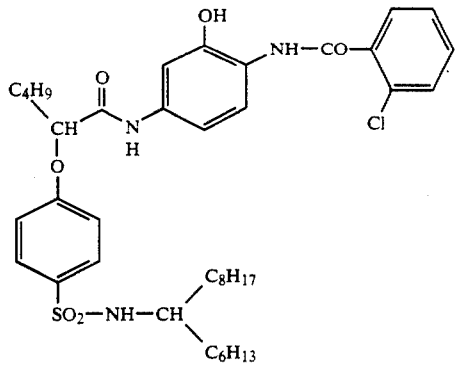
Magenta couplers
M-1
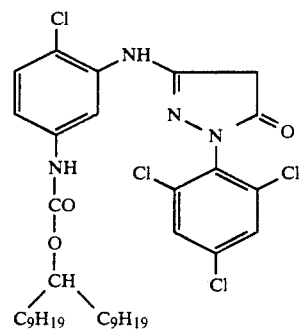
M-2
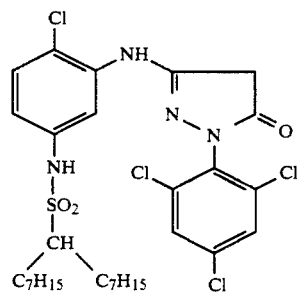
M-3
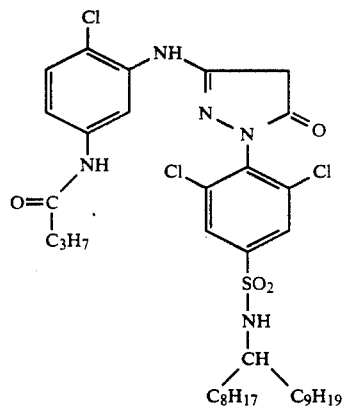
M-4
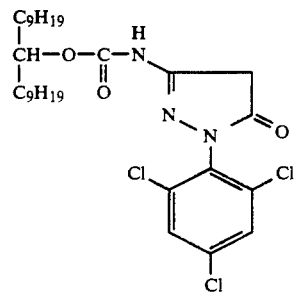
M-5
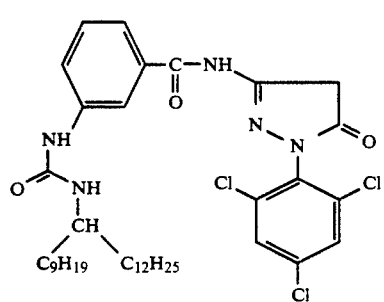
M-6
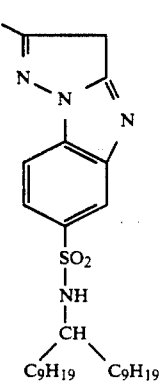

-continued
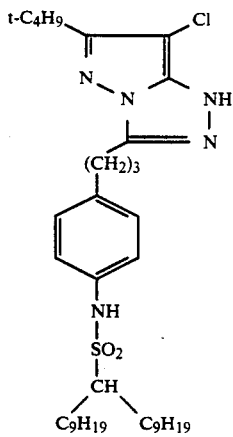
M-7
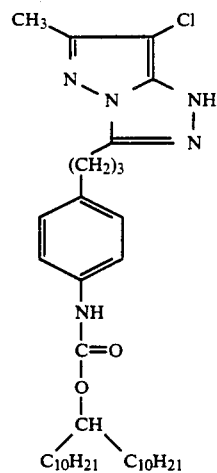
M-8
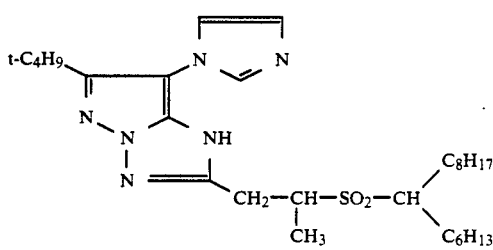
M-9
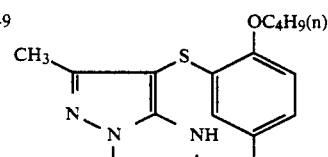
M-10
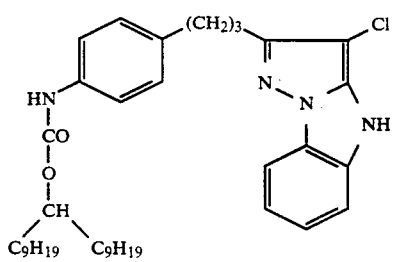
M-11
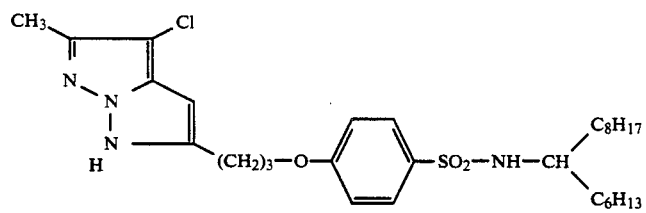
M-12
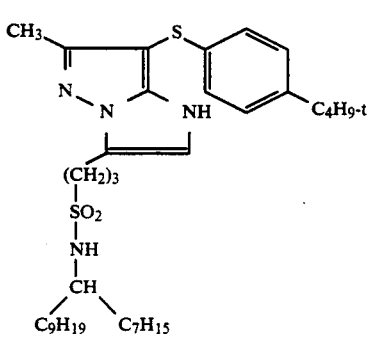
M-13
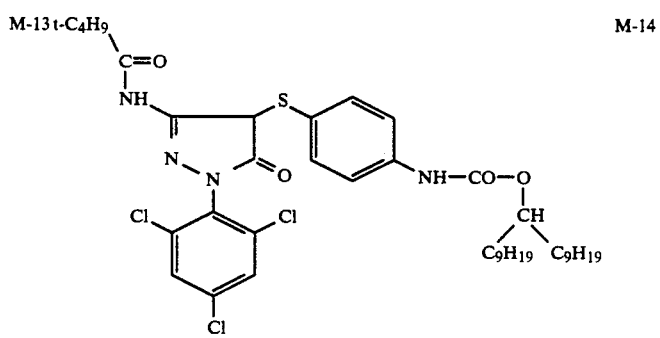
M-14

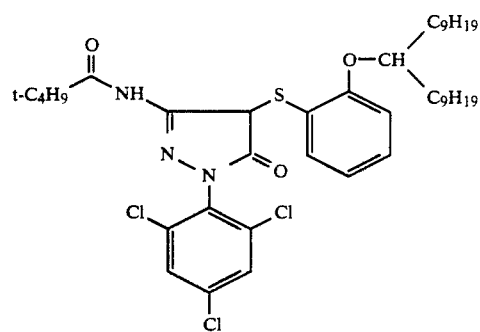
M-15
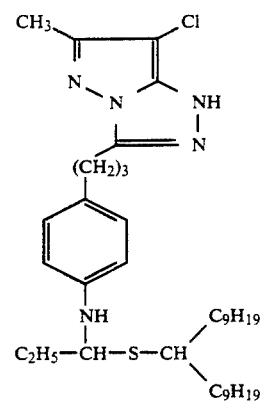
M-16
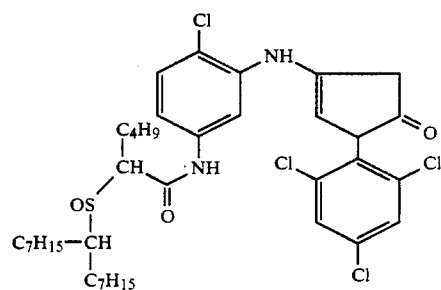
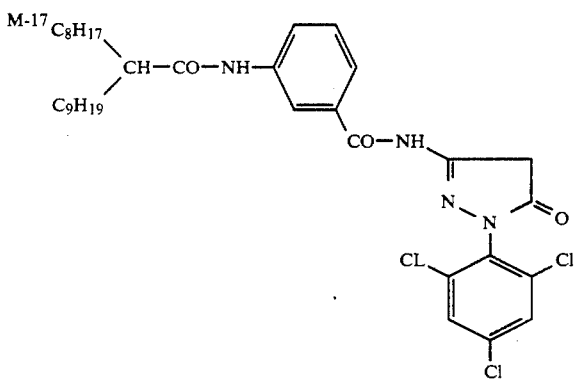
M-18
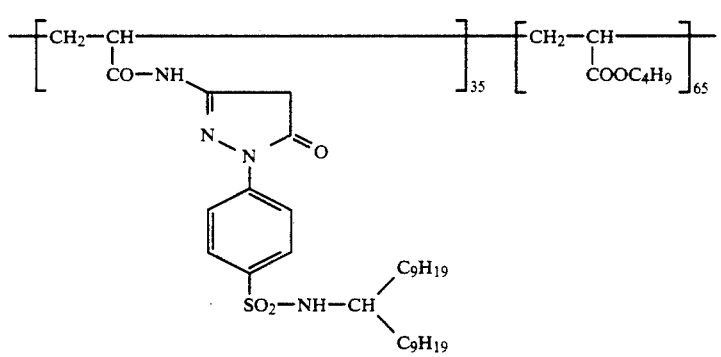
M-19
Yellow couplers
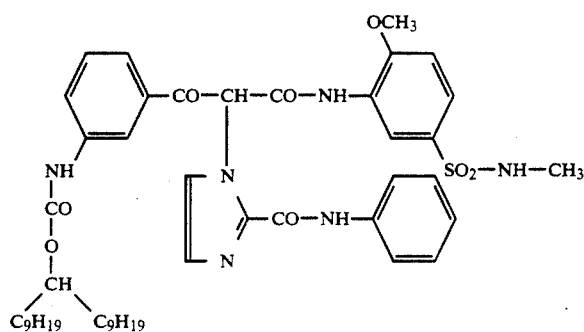
Y-1

-continued
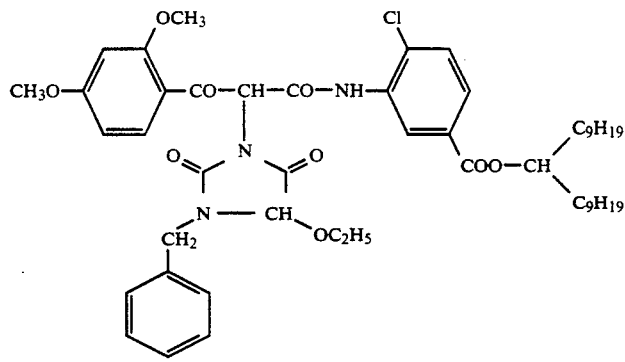
Y-2
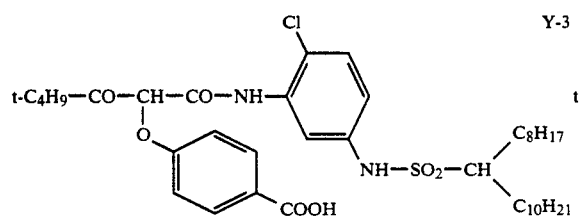
Y-3
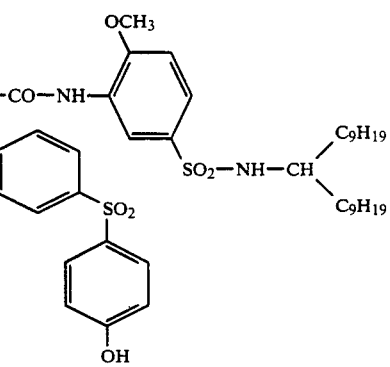
Y-4
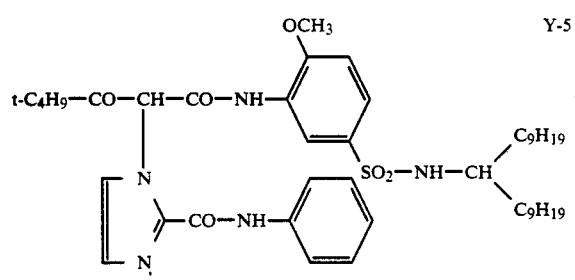
Y-5
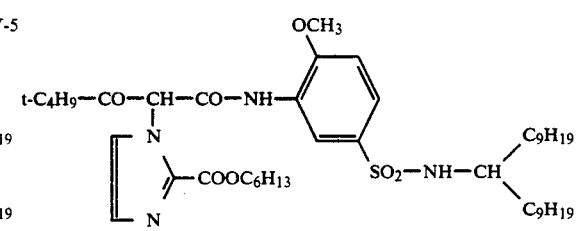
Y-6
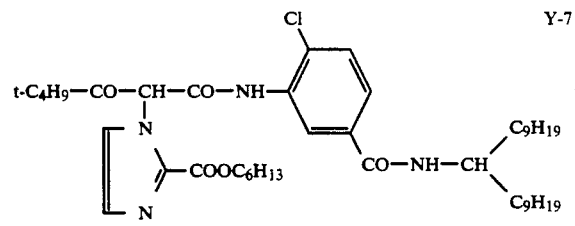
Y-7
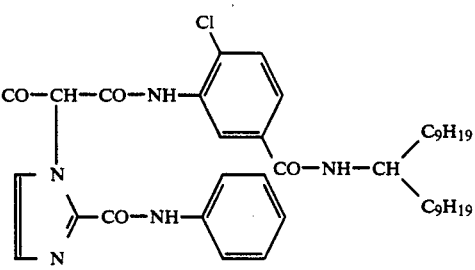
Y-8
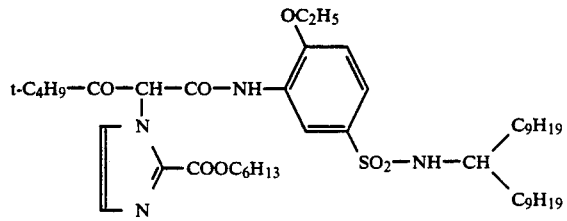
Y-9

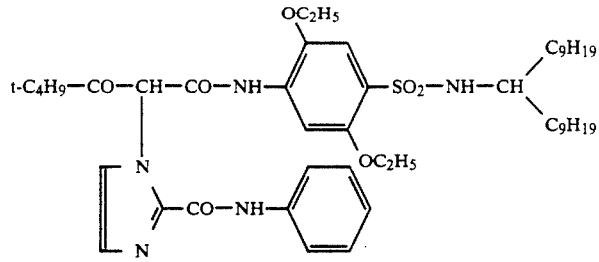
Y-10
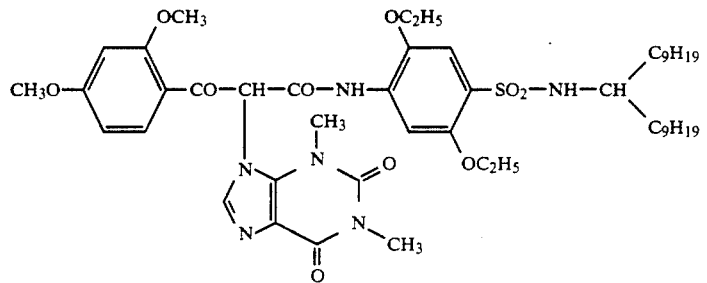
Y-11
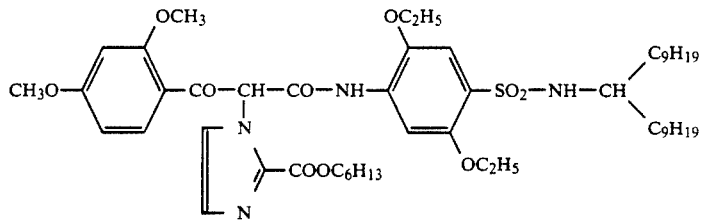
Y-12
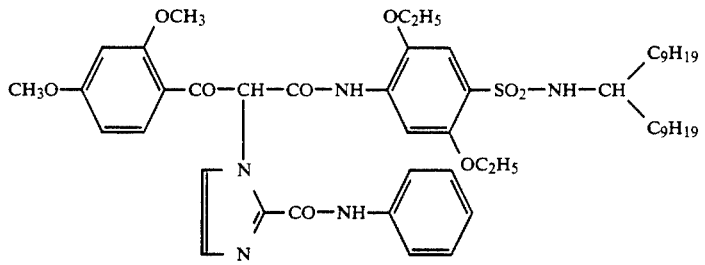
Y-13
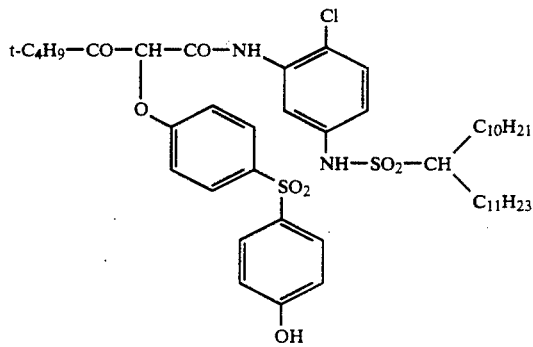
Y-14

-continued
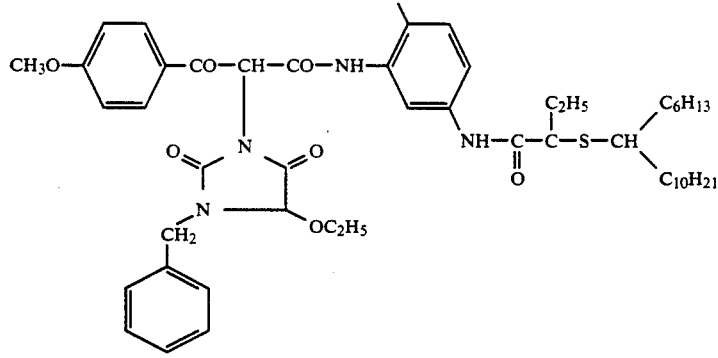 Y-15
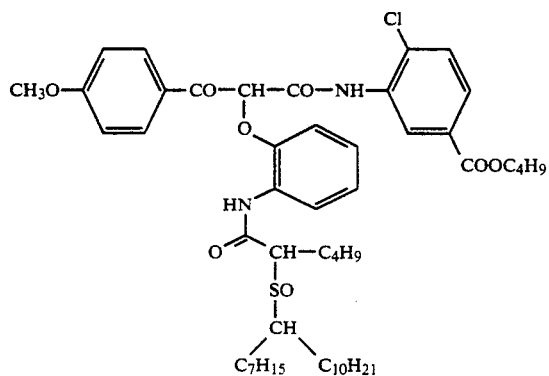 Y-16
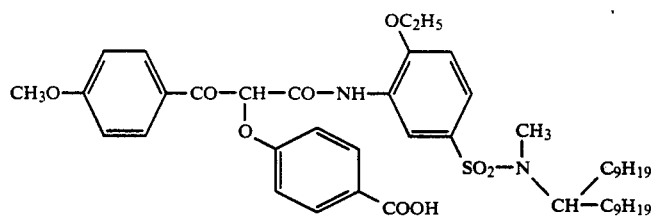 Y-17
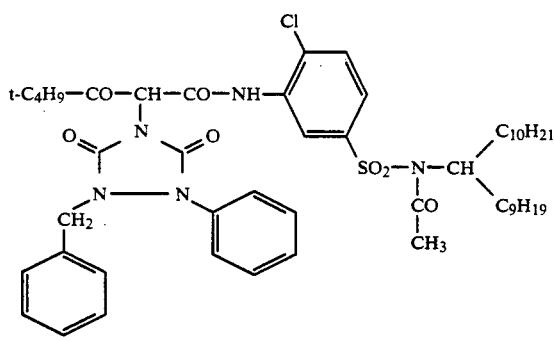 Y-18
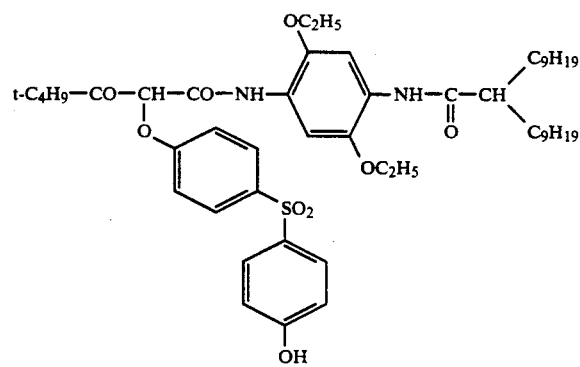 Y-19

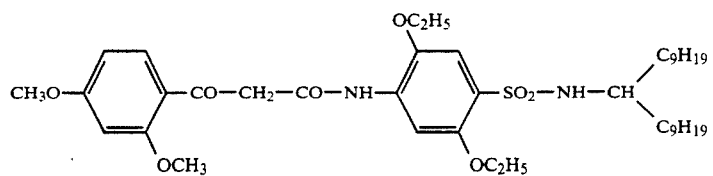
Y-20
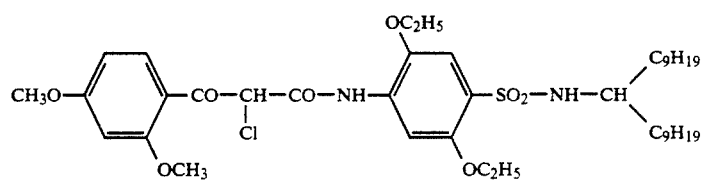
Y-21
DIR couplers
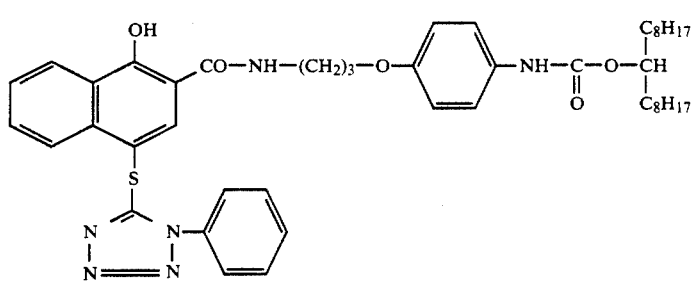
DIR-1
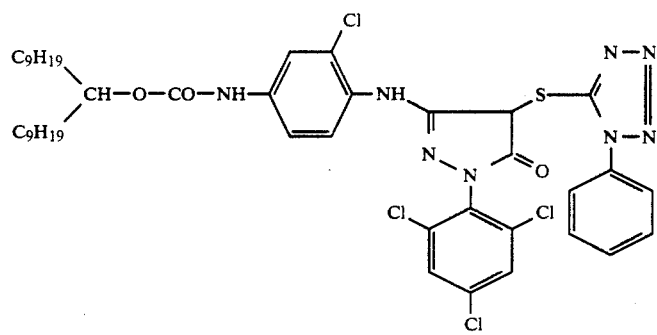
DIR-2
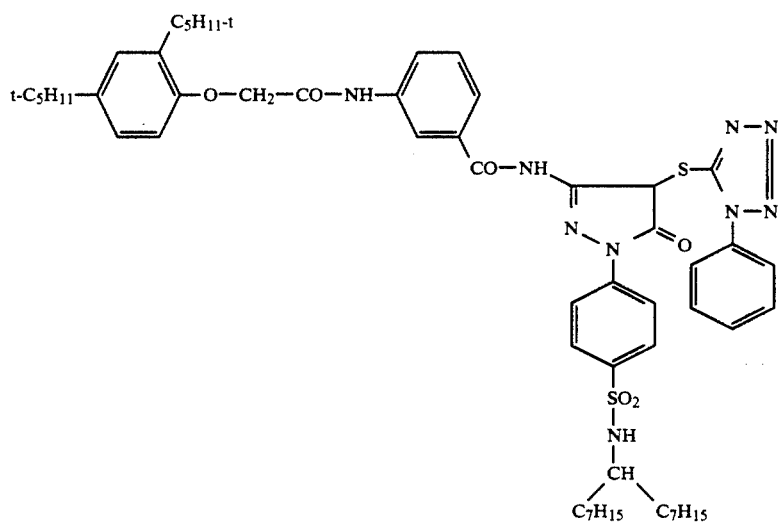
DIR-3

-continued
DIR-4
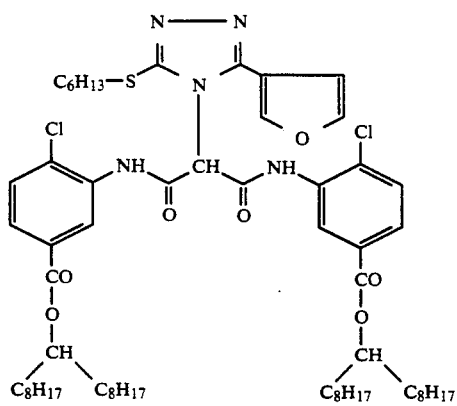
DIR-5
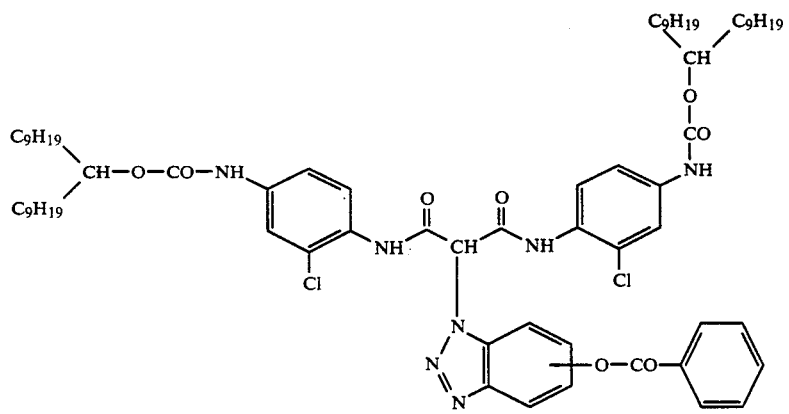
DIR-6
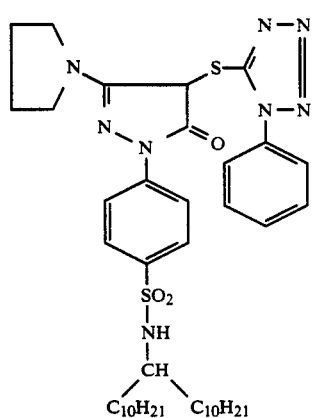
DIR-7
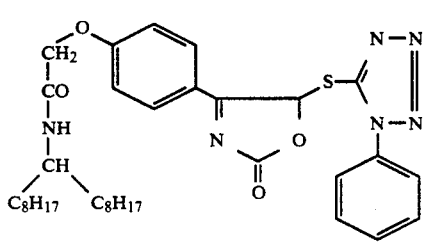
DIR-8
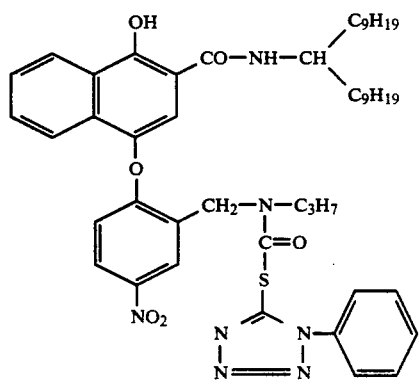
DIR-9
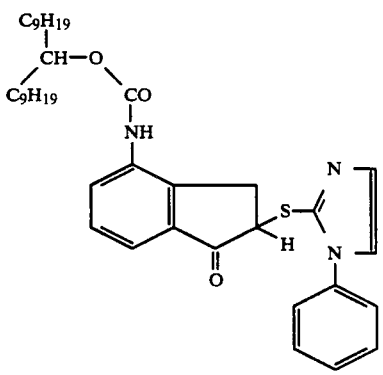
Mask couplers -continued
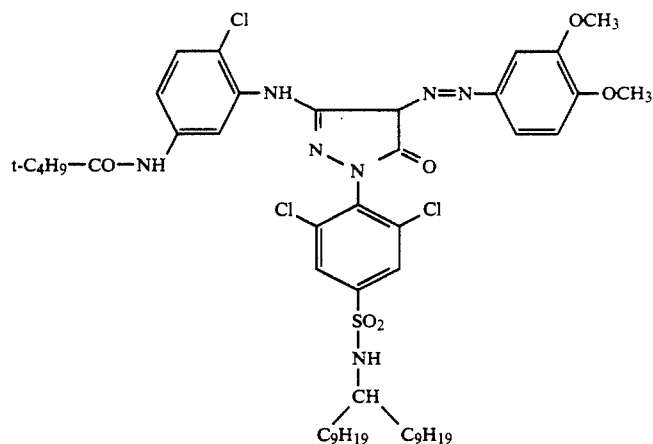
MASK-1
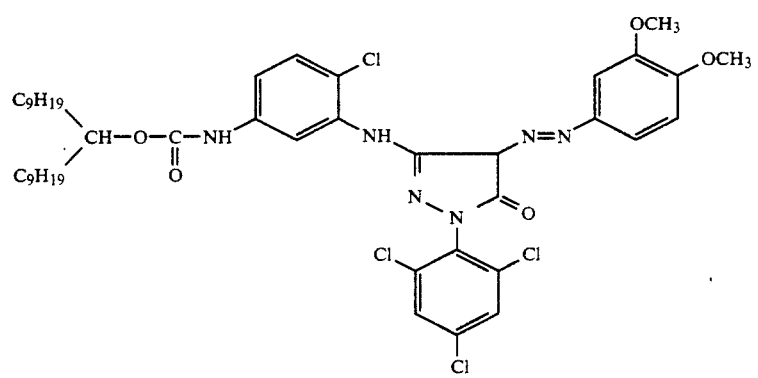
MASK-2
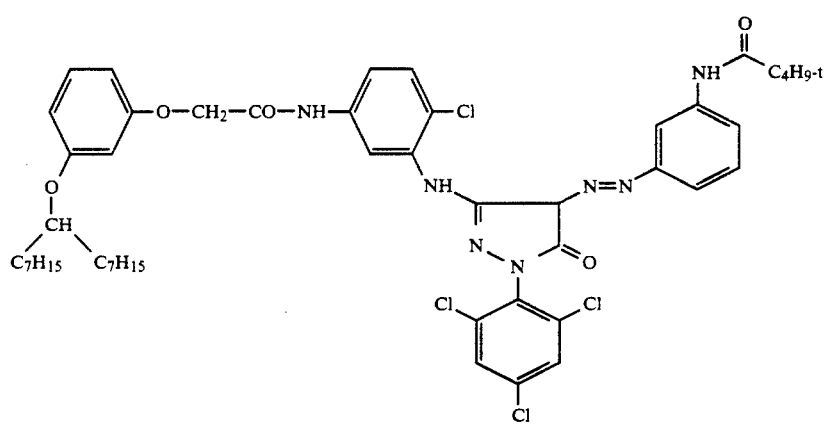
MASK-3
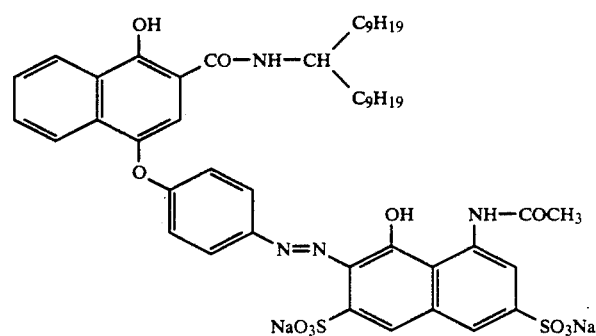
MASK-4

-continued
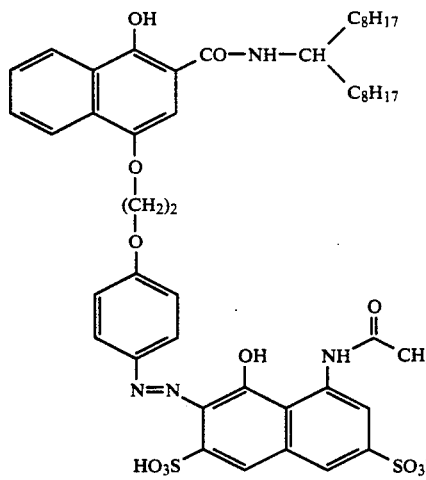
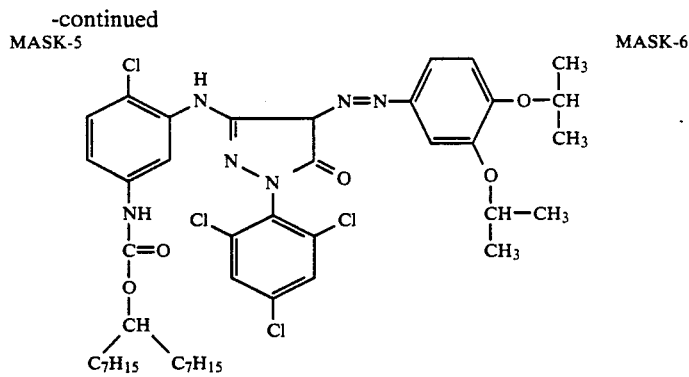
MASK-5
MASK-6
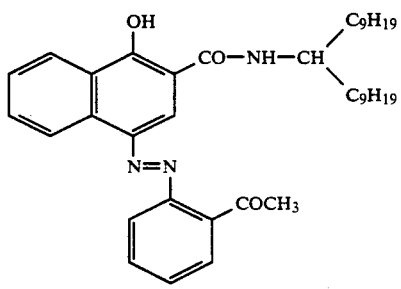
MASK-7
White couplers
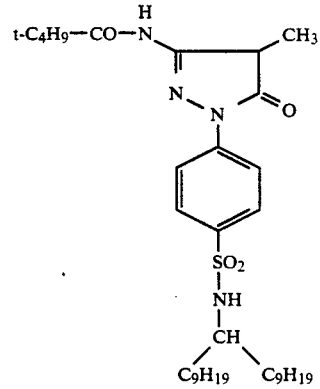
W-1
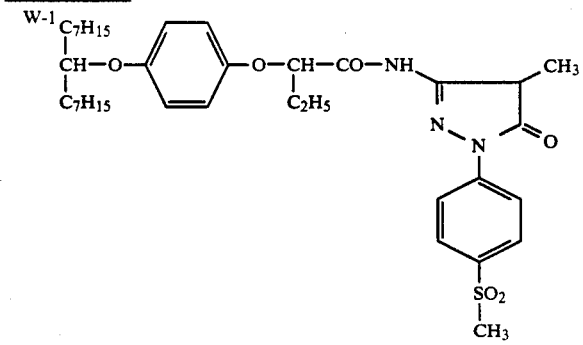
W-2
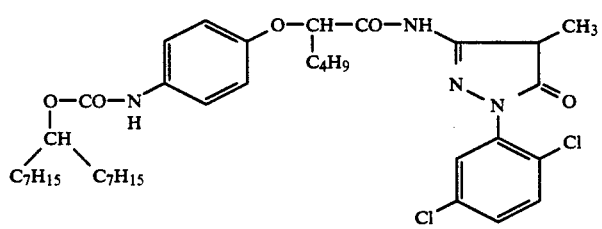
W-3
UV absorbers
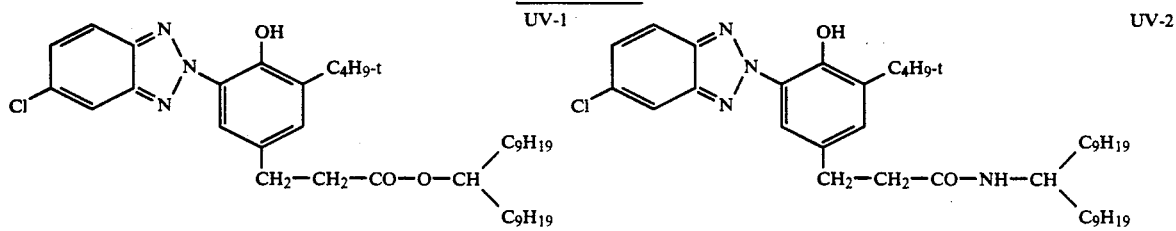
UV-1
UV-2

-continued
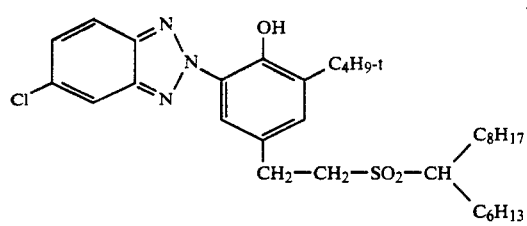 UV-3
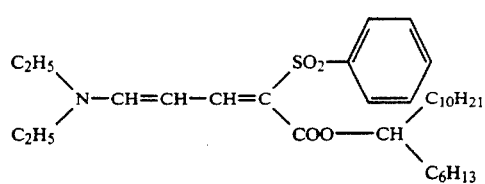 UV-4
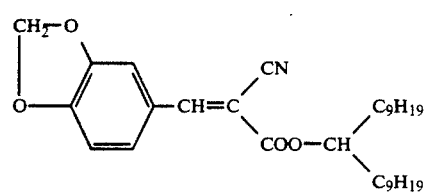 UV-5
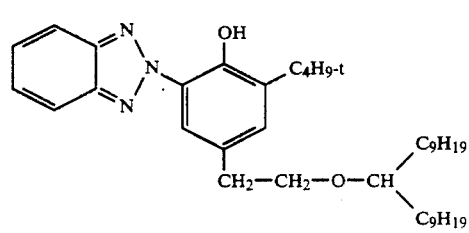 UV-6
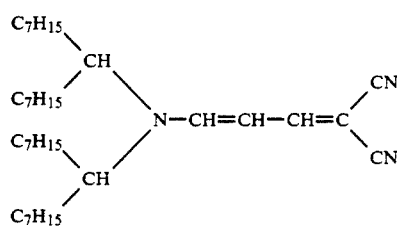 UV-7
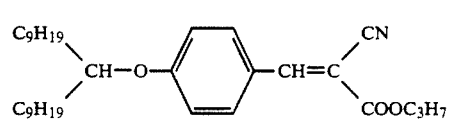 UV-8
Oil formers
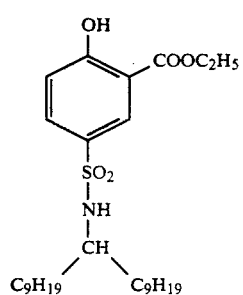 OF-1
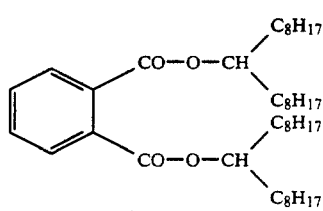 OF-2
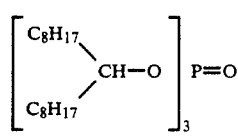 OF-3
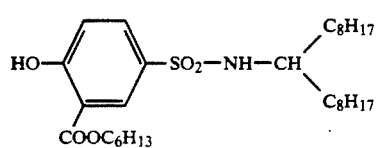 OF-4
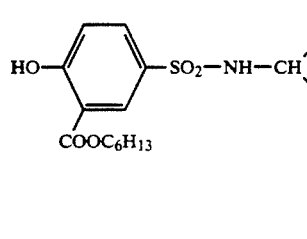 OF-5
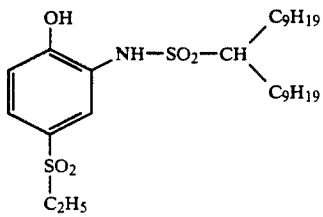 OF-6
Stabilizers

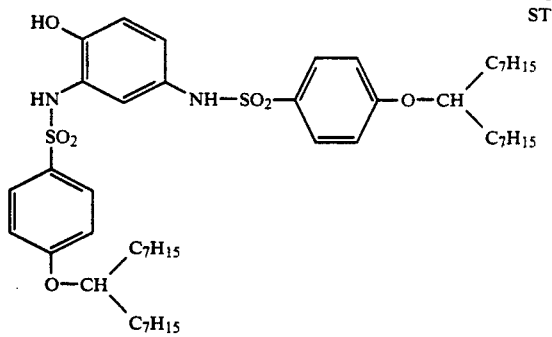

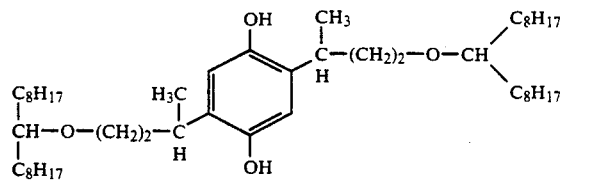

The compounds according to the invention are synthesized by known methods. The secondary alkyl radicals

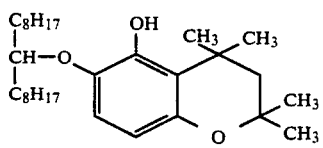

may readily be synthesized starting from the corresponding ketones:

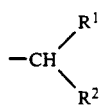

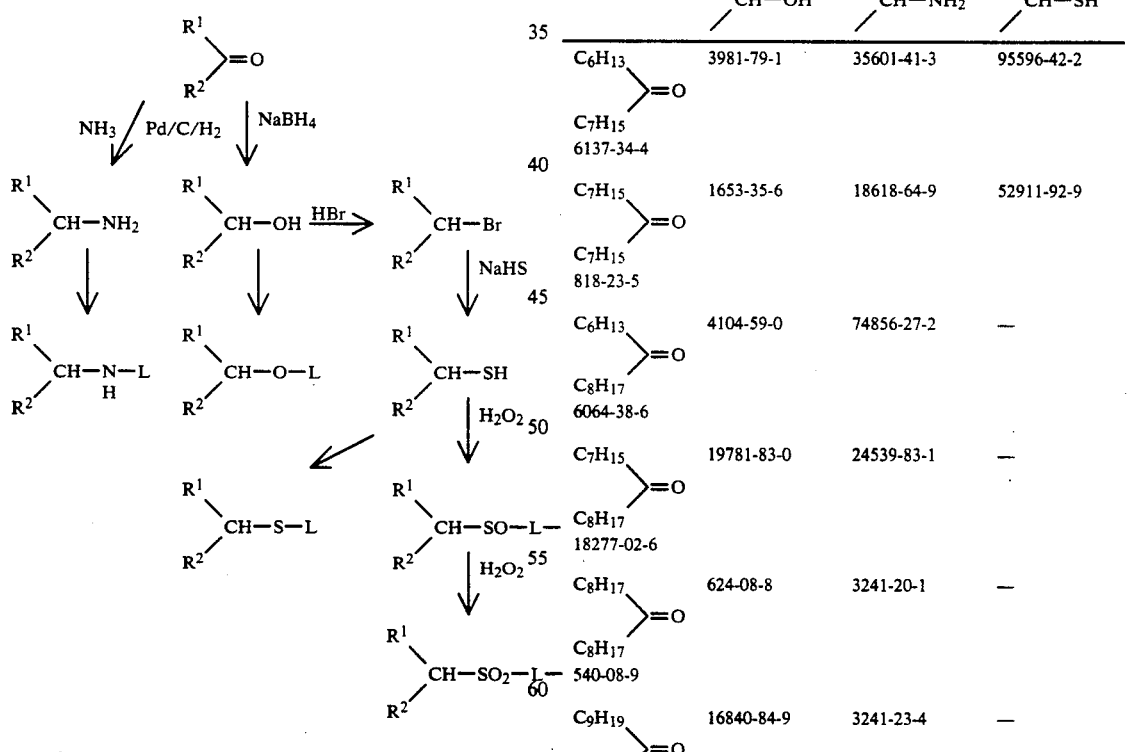

Some of the intermediate products are already known from the literature, including for example Nonadecan-7-ol : Breusch, Sohullu: B. 86, [1953] 678,683

Nonadecan-8-ol : Breusch, Sohullu: B. 86, [1953] 678,682

Nonadecan-9-ol : Breusch, Sohullu: B. 86, [1953] 678,682

Nonadecan-10-ol: Carrington, Evans: Soc. 1957, 1701,1707 Meakins, Sack: Austr. J. Scient. Res. [A] 4 [1951] 213,227

Other intermediate products may readily be researched via the following CAS registry numbers:

| | $\diagdown$CH—OH$\diagup$ | $\diagdown$CH—NH$_2$$\diagup$ | $\diagdown$CH—SH$\diagup$ |
|---|---|---|---|
| $C_6H_{13}$$\diagdown$$\diagup$=O $C_7H_{15}$ 6137-34-4 | 3981-79-1 | 35601-41-3 | 95596-42-2 |
| $C_7H_{15}$$\diagdown$$\diagup$=O $C_7H_{15}$ 818-23-5 | 1653-35-6 | 18618-64-9 | 52911-92-9 |
| $C_6H_{13}$$\diagdown$$\diagup$=O $C_8H_{17}$ 6064-38-6 | 4104-59-0 | 74856-27-2 | — |
| $C_7H_{15}$$\diagdown$$\diagup$=O $C_8H_{17}$ 18277-02-6 | 19781-83-0 | 24539-83-1 | — |
| $C_8H_{17}$$\diagdown$$\diagup$=O $C_8H_{17}$ 540-08-9 | 624-08-8 | 3241-20-1 | — |
| $C_9H_{19}$$\diagdown$$\diagup$=O $C_9H_{19}$ 504-57-4 | 16840-84-9 | 3241-23-4 | — |

Suitable intermediate products (hydroxy compounds, amines) for photographically useful compounds according to the invention in which $R^1=R^2$ can be obtained particularly readily from symmetrical ketones.

Synthesis C-1

26.4 g α-naphthol-β-carboxylic acid phenyl ester and 31 g 10-aminononadecane are boiled in 250 ml toluene. After 8 h, the toluene is distilled off and 250 xylene are added. Another 10 g 10-aminononadecane are added dropwise under reflux. After complete reaction (as determined by thin-layer chromatography), the solvent is removed in a rotary evaporator and the residue is purified by column chromatography on silica gel (eluent ethyl acetate/cyclohexane 1:10).

Yield: 10 g oil

Synthesis Y-6

100 g 10-aminononadecane are dissolved in a mixture of 700 ml dioxane and 200 ml pyridine and 88 g 3-nitro-4-methoxybenzene sulfochloride added in portions to the resulting solution. After heating for 30 minutes to 50° C., the reaction mixture is thoroughly stirred in ice/HCl and taken up in ethyl acetate. After separation, washing and drying of the ethyl acetate phase, the solvent is distilled off in vacuo. The residue is dissolved in 250 ml methanol and the resulting solution hydrogenated with 30 bar $H_2$ over Raney nickel at 30° C.

Yield: 45 g 2-methoxy-5[(10-nonadecylamino)-sulfonyl]-aniline.

44 g of this amine and 22 g pivaloyl acetic acid ethyl ester (80%) are heated in 300 ml dry toluene. After refluxing for 2 hours, a toluene/ethanol mixture is distilled off and 5 ml pivaloyl acetic acid ethyl ester in 200 ml toluene are added. After complete reaction (as determined by thin-layer chromatography), the reaction mixture is stirred into ice/HCl and taken up in ethyl acetate. After separation, washing and drying and removal of the solvent, 60 g of a colorless oil are left behind. 60 g of this oil are dissolved in 400 ml dry toluene, followed by the dropwise addition of a mixture of 7 ml sulfuryl chloride and 10 ml toluene. After complete reaction, the reaction mixture is concentrated in a rotary evaporator.

Residue: 61 g oil.

30 g of this oil are dissolved in 150 ml dimethyl acetamide and, after the addition of 14.5 g imidazole-2-carboxylic acid hexyl ester, 10 ml tetramethyl guanidine are added dropwise. After complete reaction (as determined by thin-layer chromatography), the reaction mixture is stirred into ice/HCl and taken up in ethyl acetate. After separation, washing, drying and removal of the sulfur by distillation, 31 g of an oil are left behind.

14 g high-purity coupler Y-6 are obtained therefrom by column chromatography on silica gel using ethyl acetate/ methylene chloride (1:10).

Synthesis Y-12

293 g 2,5-diethoxy acetanilide are dissolved in 1.3 l methylene chloride and 383 ml chlorosulfonic acid added dropwise to the resulting solution. The solution is stirred for 2 h at a temperature of 30° C., after which ice/HCl is added. The methylene chloride phase is separated off, washed, dried and concentrated in a rotary evaporator.

A solution of 240 g 10-aminononadecane in 240 ml methylene chloride is then added dropwise to 75 g of this sulfochloride. After stirring for 15 minutes at 40° C., the mixture is adjusted to pH 8 with 20% NaOH. After stirring for 1 hour, the organic phase is separated off, dried and the solvent distilled off in a rotary evaporator. The residue is recrystallized from acetonitrile.

Yield: 491 g.

491 g of this product are dissolved in 2.0 l n-propanol and the resulting solution is heated to the boiling temperature. After the dropwise addition of 237 ml concentrated hydrochloric acid, the mixture is stirred for 30 minutes and then stirred into ice/HCl/sodium acetate. The product is extracted with ethyl acetate, separated off, washed and dried. Removal of the solvent leaves 310 g 2-diethoxy-4-[l0-(nonadecylaminosulfonyl)]-aniline.

133 g 2,5-diethoxy-4-[10-(nonadecylaminosulfonyl)]-aniline and 70 g 2,4-dimethoxybenzoylacetic acid ester are heated to boiling temperature in 1.2 l toluene. A mixture of toluene/alcohol is distilled off and continuously replaced by dry toluene. After 10 h, the mixture is concentrated to dryness in vacuo and the residue recrystallized from methanol.

Yield 117 g Y-20. Mp.: 73° C.

117 g Y-20 are dissolved in 900 ml methylene chloride and 13 ml sulfuryl chloride are added dropwise to the resulting solution at room temperature. After removal of the solvent, the residue is recrystallized from methanol.

Yield: 96 g Y-21. Mp.: 68°–70° C.

30 g Y-21 are introduced into 250 ml dimethyl acetamide with 11.4 g imidazole-2-carboxylic acid hexyl ester, followed by the dropwise addition of 12 ml tetramethyl guanidine. After stirring for 4 h at 70° C., the reaction mixture is precipitated in ice/HCl, followed by extraction with ethyl acetate, separation, washing with water and drying. The solvent is removed in a rotary evaporator.

Residue: 30 g oily coupler Y-12.

The yellow coupler Y-12 may be obtained in highly pure form by column chromatography on silica gel using ethyl acetate/methylene chloride (1:20) as eluent. The coupler Y-12 is still not crystalline at room temperature.

Synthesis Y-13

The coupler Y-13 is similarly obtained from Y-21 using imidazole-2-carboxylic acid anilide. Y-13 is also highly pure after purification by column chromatography on silica gel using ethyl acetate/methylene chloride (1:20). It is isolated in the form of a semisolid, non-crystalline mass.

The building blocks according to the invention may be used in photographic materials of all kinds, particularly those containing photosensitive silver halide. The materials in question may be materials for black-and-white photography or color photographic materials.

Examples of photographic materials are color negative films, color reversal films, color positive films, color photographic paper, color reversal photographic paper, dyesensitive materials for the dye diffusion transfer process or the silver dye bleaching process.

Suitable supports for the production of color photographic materials are, for example, films of semisynthetic and synthetic polymers, such as cellulose nitrate, cellulose acetate, cellulose butyrate, polystyrene, polyvinyl chloride, polyethylene terephthalate and polycarbonate, and paper laminated with a baryta layer or α-olefin polymer layer (for example polyethylene). These supports may be dyed with dyes and pigments, for example titanium dioxide. They may also be dyed black for the purpose of screening against light. The surface of the support is generally subjected to a treatment to improve the adhesion of the photographic emulsion layer, for example to a corona discharge with subsequent application of a substrate layer.

The color photographic materials normally contain at least one red-sensitive silver halide emulsion layer, at least one green-sensitive silver halide emulsion layer and at least one blue-sensitive silver halide emulsion layer respectively containing spectrally associated color couplers and, optionally, intermediate layers and protective layers.

Gelatine is preferably used as binder although it may be completely or partly replaced by other synthetic, semisynthetic or even naturally occurring polymers. Synthetic gelatine substitutes are, for example, polyvinyl alcohol, poly-N-vinyl pyrrolidone, polyacrylamides, polyacrylic acid and derivatives thereof, particularly copolymers. Naturally occurring gelatine substitutes are, for example, other proteins, such as albumin or casein, cellulose, sugar, starch or alginates. Semisynthetic gelatine substitutes are generally modified natural products. Cellulose derivatives, such as hydroxyalkyl cellulose, carboxymethyl cellulose, and phthalyl cellulose and also gelatine derivatives which have been obtained by reaction with alkylating or acylating agents or by grafting on of polymerizable monomers are examples of such modified natural products.

The binders should contain an adequate number of functional groups, so that sufficiently resistant layers can be produced by reaction with suitable hardeners. Functional groups of the type in question are, in particular, amino groups and also carboxyl groups, hydroxyl groups and active methylene groups.

The gelatine preferably used may be obtained by acidic or alkaline digestion. Oxidized gelatine may also be used. The production of such gelatines is described, for example, in The Science and Technology of Gelatine, edited by A. G. Ward and A. Courts, Academic Press 1977, pages 295 et seq. The particular gelatine used should contain as few photographically active impurities as possible (inert gelatine). Gelatines of high viscosity and low swelling are particularly advantageous.

The silver halide present as photosensitive constituent in the photographic emulsion may contain as halide chloride, bromide or iodide and mixtures thereof. For example, 0 to 15 mol-% of the halide of at least one layer may consist of iodide, 0 to 100 mol-% of chloride and 0 to 100 mol-% of bromide. Silver bromide iodide emulsions are normally used in the case of color negative and color reversal films while silver bromide emulsions or silver chloride bromide emulsions of high chloride content up to pure silver chloride emulsions are normally used in the case of color negative and color reversal paper. The silver halide may consist of predominantly compact crystals which may have, for example, a regular cubic or octahedral form or transitional forms. However, the silver halide may also consist with advantage of platelet-like crystals of which the average diameter-to-thickness ratio is preferably at least 5:1, the diameter of a crystal being defined as the diameter of a circle with an area corresponding to the projected area of the crystal. However, the layers may also contain platy silver halide crystals in which the diameter-to-thickness ratio is considerably greater than 5:1, for example from 12:1 to 30:1.

The silver halide grains may also have a multiplelayer grain structure, in the most simple case with an inner and an outer core region (core/shell), the halide composition and/or other modifications such as, for example, doping of the individual grain regions, being different. The average grain size of the emulsions is preferably between 0.2 $\mu$m and 2.0 $\mu$m; the grain size distribution may be both homodisperse and heterodisperse. A homodisperse grain size distribution means that 95% of the grains differ from the average grain size by no more than $\pm 30\%$. In addition to the silver halide, the emulsions may also contain organic silver salts, for example silver benztriazolate or silver behenate.

The silver halide emulsion is generally subjected to chemical sensitization under defined conditions (pH, pAg, temperature, gelatine, silver halide and sensitizer concentration) until sensitivity and fogging are both optimal. The process is described, for example, in H. Frieser "Die Grundlagen der Photographischen Prozesse mit Silberhalogeniden", pages 675-734, Akademische Verlagsgesellschaft (1968).

The photographic emulsions may contain compounds to prevent fogging or to stabilize the photographic function during production, storage and photographic processing.

The photographic emulsions may be spectrally sensitized using methine dyes or other dyes. Particularly suitable dyes are cyanine dyes, merocyanine dyes and complex merocyanine dyes.

A review of the polymethine dyes suitable as spectral sensitizers, suitable combinations thereof and supersensitizing combinations thereof can be found in Research Disclosure 17643/1978, Section IV.

There is no need for sensitizers where the natural sensitivity of the silver halide is sufficient for a certain spectral region, for example the blue sensitivity of silver bromides.

Non-diffusing monomeric or polymeric color couplers are associated with the differently sensitized emulsion layers and may be arranged in the same layer or in an adjacent layer. Cyan couplers are normally associated with the red-sensitive layers, magenta couplers with the green-sensitive layers and yellow couplers with the blue-sensitive layers.

The couplers or other compounds may be incorporated in silver halide emulsion layers by initially preparing a solution, a dispersion or an emulsion of the particular compound and then adding it to the casting solution for the particular layer. The choice of a suitable solvent or dispersant depends upon the particular solubility of the compound. By virtue of their excellent solubility, the building blocks according to the invention may be processed and introduced into the layers as an emulsion.

Hydrophobic compounds may also be introduced into the casting solution using high-boiling solvents, so-called oil formers. Corresponding methods are described, for example in U.S. Pat. No. 2,322,027, U.S. Pat. No. 2,801,170, U.S. Pat. No. 2,801,171 and EP-A-0 043 037.

Instead of using high-boiling solvents, it is also possible to use oligomers or polymers, so-called polymeric oil formers.

The compounds may also be introduced into the casting solution in the form of charged latices, cf. for example DE-A-25 41 230, DE-A-25 41 274, DE-A-28 35 856, EP-A-0 014 921, EP-A-0 069 671, EP-A-0 130 115, U.S. Pat. No. 4,291,113.

Suitable oil formers are, for example, phthalic acid alkyl esters, phosphonic acid esters, phosphoric acid esters, citric acid esters, benzoic acid esters, amides, fatty acid esters, trimesic acid esters, alcohols, phenols, aniline derivatives and hydrocarbons.

Examples of suitable oil formers are dibutyl phthalate, dicyclohexyl phthalate, di-2-ethyl hexyl phthalate, decyl phthalate, triphenyl phosphate, tricresyl phosphate, 2-ethyl hexyl diphenyl phosphate, tricyclohexyl phosphate, tri-2-ethyl hexyl phosphate, tridecyl phosphate, tributoxyethyl phosphate, trichloropropyl phosphate, di-2-ethyl hexyl phenyl phosphate, 2-ethyl hexyl benzoate, dodecyl benzoate, 2-ethyl hexyl-p-hydroxybenzoate, diethyl dodecaneamide, N-tetradecyl pyrrolidone, isostearyl alcohol, 2,4-di-tert-amylphenol, dioctyl acetate, glycerol tributyrate, isostearyl lactate, trioctyl citrate, N,N-dibutyl-2-butoxy-5-tert.-octyl aniline, paraffin, dodecylbenzene and diisopropyl naphthalene. Instead of these oil formers, it is also possible with advantage to use the oil formers corresponding to formula I.

EXAMPLE 1

Comparison of coupler C-1 with comparisons CC-1 and CC-2

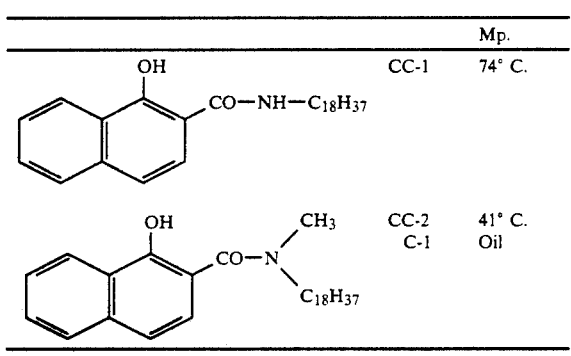

Quantities of 8 mmol coupler were dissolved in a ratio of 1:3 in ethyl acetate (EA) heated to approximately 50° C., after which dibutyl phthalate (DBP) and manoxol were added to the resulting solution so that a ratio of coupler to DBP to EA to manoxol of 1:1:3:0.1 was obtained. The solution was then emulsified in 7.5% gelatine solution. A ratio of coupler to gelatine of approximately 1:2 is obtained, depending on the molecular weight. The emulsion was stirred for 6 minutes at 1000 r.p.m., undergoing an increase in temperature to around 50° C.; EA was distilled off under suction in a water jet vacuum (200-300 mbar).

The quality of the fresh coupler emulsions was evaluated as follows using a phase contrast or polarization microscope:
a) Particle size
 1 = very fine (<0.5 μm)
 2 = fine (<1 μm)
 3 = fine with some larger particles
 4 = medium
 5 = coarse
b) Homogeneity
 1 = no crystals discernible
 2 = some crystals discernible
 3 = many crystals discernible
 4 = extensive crystallization The same evaluation was made after the emulsions had been intensively stirred for 3 h and 6 h at 50° C.

TABLE 1

| | Quality of coupler emulsions | | | | | |
|---|---|---|---|---|---|---|
| | Fresh | | 3 h/50° C. | | 6 h/50° C. | |
| | a | b | a | b | a | b |
| CC-1 | 1 | 2 | 3 | 3 | 4 | 4 |
| CC-2 | 2 | 2 | 2 | 2 | 2 | 3 |
| C-1 | 1 | 1 | 1 | 1 | 1 | 1 |

By virtue of its lower solidus point, an emulsion of C-1 can be prepared without an oil former. By contrast, CC-1 crystallizes out in oil-former-free emulsions during the production of a photographic layer, resulting in matt layers having a rough surface.

EXAMPLE 2

Comparison of various yellow couplers

| | | Mp. |
|---|---|---|
| Y-6 | | oil |
| Y-10 | | oil |
| Y-12 | | oil |
| Y-13 | | semi-solid |
| VY-1 | | 67° C. |

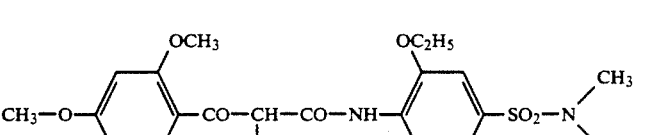

-continued

| | | | Mp. |
|---|---|---|---|
| VY-2 | CH₃—O—[benzene with OCH₃]—CO—CH(—N[pyrazole]—COOC₆H₁₃)—CO—NH—[benzene with OC₂H₅, OC₂H₅]—SO₂—N(CH₃)(C₁₈H₃₇) | | 57° C. |

The advantage of the compounds according to the invention can clearly be seen simply by comparing the melting points. In addition, the compounds Y-6, Y-10, Y-12, Y-1 3 are distinguished by distinctly better solubility in tricresyl phosphate and dibutyl phthalate.

The compounds mentioned were emulsified as in Example 1 and the coupler emulsions obtained visually evaluated as described in Example 1.

TABLE 2

| | Quality of coupler emulsions | | | | | |
|---|---|---|---|---|---|---|
| | Fresh | | After 3 h/50° C. | | After 6 h/50° C. | |
| | a | b | a | b | a | b |
| Y-6 | 1 | 1 | 1 | 1 | 1 | 2 |
| Y-10 | 1 | 2 | 1 | 2 | 1 | 2 |
| Y-12 | 1 | 1 | 1 | 1 | 1 | 1 |
| Y-13 | 1 | 1 | 1 | 2 | 1 | 1 |
| CY-1 | 3 | 3 | 3 | 3 | 3 | 4 |
| CY-2 | 4 | 3 | 4 | 4 | 4 | 4 |

Emulsions prepared in accordance with Example 1 were mixed with a silver bromide iodide emulsion (0.7 mol-% a ratio of 1 mol coupler to 5.2 mol AgNO₃ and the iodide) in resulting mixture was applied to a layer support of cellulose acetate and overcoated with a protective layer of a 3% gelatine solution containing a carbamoyl pyridinium betaine (CAS Reg. No. 65411-60-1) as hardener. After drying and cutting, the samples thus prepared were exposed behind a step wedge and processed as follows with and without benzyl alcohol (30° C.):

| Development | 210 s |
|---|---|
| Bleaching/fixing | 90 s |
| Rinsing | 120 s |

The baths had the following composition:
5.0 g 4-amino-3-methyl-N-ethyl-N-(B-methanesulfonamidoethyl)-aniline sulfate
(15.0 ml benzyl alcohol)
2.5 g sodium hexametaphosphate
1.85 g Na₂SO₃ sicc.
1 4 g NaBr
0.5 g KBr
39.1 g borax
make up with water to 1000 ml, adjust to pH 10.3 with NaOH.
Bleaching/fixing bath:
50.0 g ethylenediaminetetraaceticacid/iron(III)/ammonium complex
50.0 ml (NH₄)₂SO₃, 40% solution
140.0 ml (NH₄)₂SSO₃, 70% solution
20.0 ml aqueous ammonia, 28%
4.0 g ethylenediamine tetraacetic acid make up with water to 1000 ml.

The relative sensitivity and maximum color density of each of the samples prepared are shown in Table 3. Relative values based on the highest sensitivity obtained (=100) are shown for sensitivity. The values obtained where development was carried out in the presence of benzyl alcohol are shown in brackets.

TABLE 3

| | Rel. sensitivity | D_max | CY without benzyl alcohol |
|---|---|---|---|
| CY-1 | 85 | (94) | 1.5 (2.0) | 1.0 |
| CY-2 | 87 | (93) | 1.6 (2.1) | 1.06 |
| Y-6 | 96 | (97) | 2.5 (2.5) | 1.66 |
| Y-10 | 99 | (100) | 2.6 (2.7) | 1.73 |
| Y-12 | 98 | (98) | 2.8 (2.8) | 1.86 |
| Y-13 | 98 | (98) | 2.4 (2.4) | 1.60 |

The couplers according to the invention are distinguished by a distinctly higher maximal density in developers containing benzyl alcohol. Above all, however, this higher density is maintained, even in developers free from benzyl alcohol. This is of considerable future importance in ecological terms for new processing techniques. In addition, the improved color yield CY provides for a considerable saving of silver.

I claim:

1. A photographic recording element comprising at least one photosensitive silver halide emulsion layer arranged on a layer support and, optionally, other non-photosensitive binder layers, wherein in a photosensitive or non-photosensitive layer, the element contains at least one organic oil former compound which does not produce an image dye corresponding to the following formula

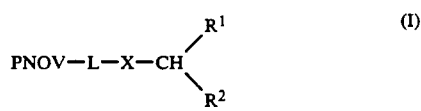

$$PNOV-L-X-CH\begin{matrix}R^1\\R^2\end{matrix} \quad (I)$$

in which
PNOV is the residue of a photographically useful oil former which does not produce an image dye;
L and X combined represent —NH—SO₂—; and
R¹ and R² are unbranched alkyl radicals containing at least 6 C atoms, with the proviso that R¹ and R₂ together contain at least 14 C atoms.

2. A photographic recording element comprising at least one photosensitive silver halide emulsion layer arranged on a layer support and, optionally, other non-photosensitive binder layers, wherein in a photosensitive or non-photosensitive layer, the element contains at least one organic oil former compound which does not produce an image dye corresponding to the following formula

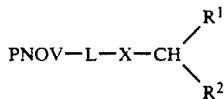 (I)

in which
PNOV is the residue of a photographically useful oil former which does not produce an image dye;
L and X combined represent the following formula

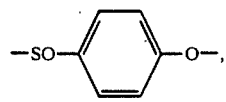

and
$R^1$ and $R_2$ are unbranched alkyl radicals containing at least 6 C atoms, with the provisio that $R^1$ and $R_2$ together contain at least 14 C atoms.

3. A photographic recording element comprising at least one photosensitive silver halide emulsion layer arranged on a layer support and, optionally, other non-photosensitive binder layers, wherein in a photosensitive or non-photosensitive layer, the element contains at least one organic oil former compound which does not produce an image dye corresponding to the following formula

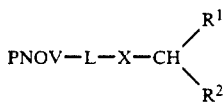 (I)

in which
PNOV is the residue of a photographically useful oil former which does not produce an image dye;
L and X combined represent $-SO_2-NH-$, and
$R^1$ and $R_2$ are unbranched alkyl radicals containing at least 6 C atoms, with the provisio that $R^1$ and $R^2$ together contain at least 14 C atoms.

4. A photographic recording element comprising at least one photosensitive silver halide emulsion layer arranged on a layer support and, optionally, other non-photosensitive binder layers, wherein in a photosensitive or non-photosensitive layer, the element contains at least one organic oil former compound which does not produce an image dye corresponding to the following formula

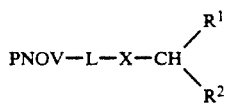 (I)

in which
PNOV is the residue of a photographically useful oil former which does not produce an image dye;
L and X combined represent

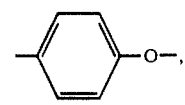

and
$R^1$ and $R^2$ are unbranched alkyl radicals containing at least 6 C atoms, with the provisio that $R^1$ and $R^2$ together contain at least 14 C atoms.

* * * * *